United States Patent
Watanabe

(10) Patent No.: US 7,549,798 B2
(45) Date of Patent: Jun. 23, 2009

(54) RADIOGRAPHIC IMAGING APPARATUS, IMAGING UNIT AND RADIOGRAPHIC IMAGING SYSTEM

(75) Inventor: Tetsuo Watanabe, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 14 days.

(21) Appl. No.: 11/872,314

(22) Filed: Oct. 15, 2007

(65) Prior Publication Data

US 2008/0095324 A1    Apr. 24, 2008

(30) Foreign Application Priority Data

Oct. 18, 2006   (JP)   .............................. 2006-283931

(51) Int. Cl.
*H01J 31/49* (2006.01)
(52) U.S. Cl. ..................................... 378/189
(58) Field of Classification Search .................. 378/114, 378/117, 167–170, 173, 181, 182, 184–192, 378/204, 210; 250/363.05, 363.08, 370.09, 250/370.11

See application file for complete search history.

(56) References Cited

U.S. PATENT DOCUMENTS

| | | | |
|---|---|---|---|
| 6,412,978 B1 * | 7/2002 | Watanabe et al. | 378/197 |
| 2004/0252613 A1 * | 12/2004 | Iwakiri | 369/53.12 |
| 2006/0120512 A1 * | 6/2006 | Watanabe | 378/198 |
| 2008/0159486 A1 * | 7/2008 | Hesl et al. | 378/189 |

FOREIGN PATENT DOCUMENTS

| | | | | |
|---|---|---|---|---|
| DE | WO2006056563 A1 | * | 6/2006 | |
| JP | 2005-000470 | | 1/2005 | |

\* cited by examiner

*Primary Examiner*—Edward J Glick
*Assistant Examiner*—Mona M Sanei
(74) *Attorney, Agent, or Firm*—Canon U.S.A., Inc. I.P. Division

(57) ABSTRACT

A radiographic imaging apparatus includes a holding unit which detachably holds an imaging unit for detecting radiation generated by a radiation generation unit and acquiring a radiographic image, a detachment restriction unit which restricts detachment of the imaging unit from the holding unit, and a controller which cancels the restriction by the detachment restriction unit when a grip detection unit for detecting gripping of the imaging unit detects the gripping on the imaging unit.

6 Claims, 8 Drawing Sheets

RADIOGRAPHIC IMAGING APPARATUS, IMAGING UNIT AND RADIOGRAPHIC IMAGING SYSTEM

BACKGROUND OF THE INVENTION

1. Field of the Invention

The present invention relates to a radiographic imaging apparatus, an imaging unit and a radiographic imaging system.

2. Description of the Related Art

The recent progress of digital technologies is popularizing a radiographic imaging apparatus which converts a radiographic image into an electrical signal, processes the electrical signal, and reproduces it on, e.g., a CRT as a visible image, thereby obtaining a high-quality radiographic image.

FIG. 7 is a conceptual view of a radiographic imaging system using the above-described radiographic imaging apparatus. A radiographic imaging apparatus 1 arranged in front of an object P incorporates a radiation detection sensor 2. A radiation generator 3 arranged behind the object P generates radiation and irradiates the object P with it. The radiation transmitted through the object P changes to visible light through the phosphor of the radiation detection sensor 2. Photoelectric conversion elements arrayed in a two-dimensional matrix detect the light as an electrical image signal. A controller 4 to control electrical signal readout from the radiation detection sensor 2 and image transfer to a monitor 5 is connected to the radiographic imaging apparatus 1. The controller 4 digitally processes the image signal read out from the radiation detection sensor 2 and displays the radiographic image of the object P on the monitor 5.

This imaging system includes a detection panel set on a frame dedicated to a specific imaging form such as a standing position or lying position and is selectively used as needed. The system is generally stationary installed in a radiographic examination room.

A recently developed portable X-ray detection unit is used when imaging in an arbitrary posture is necessary. Japanese Patent Laid-Open No. 2005-470 proposes an X-ray imaging apparatus using a portable X-ray detection unit. The X-ray imaging apparatus can stationary be supported at a position opposing the X-ray tube or separated from the support unit.

The former case allows easy positioning and quick accurate alignment. The latter case allows to place the X-ray detection unit at an arbitrary position. It is therefore possible to reduce the burden on an immovable object and take an image while adjusting the X-ray imaging apparatus to the position of the object. That is, the single X-ray imaging apparatus can cope with two imaging forms, and the convenience improves.

FIG. 8 is a view showing the arrangement of a general mobile C-arm radiographic imaging apparatus 11. A C-shaped arm member 14 is attached to the distal end of a horizontal shaft 13 supported on a main body unit 12. The arm member 14 can rotate and move as indicated by arrows. The arm member 14 has, at two ends, an X-ray generation unit 15 and an X-ray detection unit 17 opposing it and detachably attached to a holder unit 16. The arm member 14 is positioned in an arbitrary posture and used.

The X-ray detection unit 17 can take an arbitrary posture determined by rotation Rh about a horizontal shaft and rotation Rs along the track of the arm member 14 itself. Hence, the X-ray detection unit 17 takes an arbitrary posture when being detached from the holder unit 16. It is necessary to execute the operation after the posture of the arm member 14 returns to a position to easily detach the X-ray detection unit 17.

However, the above-described mobile C-arm radiographic imaging apparatus 11 may erroneously drop the X-ray detection unit 17 if its detachment direction matches the direction of gravity.

SUMMARY OF THE INVENTION

It is an object of the present invention to solve the above-described problem and provide a radiographic imaging apparatus capable of safely and easily detaching an imaging unit even when it takes an arbitrary posture by setting a support unit.

According to the first aspect of the present invention, there is provided a radiographic imaging apparatus which comprises a holding unit which holds an imaging unit for detecting radiation generated by a radiation generation unit and acquiring a radiographic image, a detachment restriction unit which restricts detachment of the imaging unit from the holding unit, and a controller which cancels the restriction by the detachment restriction unit when a grip detection unit for detecting gripping of the imaging unit detects the gripping on the imaging unit.

According to the second aspect of the present invention, there is provided an imaging unit for acquiring a radiographic image which comprises a grip unit having a sensor for user's gripping, and an output unit which outputs a signal to a controller for releasing a lock of a radiation detection sensor.

According to the third aspect of the present invention, there is provided a radiographic imaging system which comprises a holding unit which holds an imaging unit for detecting radiation generated by a radiation generator and acquiring a radiographic image, and a restriction unit which has a first restriction mode to restrict detachment of the imaging unit for acquiring a radiographic image in a direction parallel to an image reception area of the imaging unit and a second restriction mode to restrict detachment of the imaging unit in a direction perpendicular to the image reception area of the imaging unit.

Further features of the present invention will become apparent from the following description of exemplary embodiments with reference to the attached drawings.

DESCRIPTION OF THE EMBODIMENTS

The embodiments of the present invention will be described in detail with reference to FIGS. 1 to 6. Radiation includes electromagnetic waves such as X-rays, α-rays, β-rays, and γ-rays. A radiographic imaging apparatus according to each embodiment is applicable to the radiographic imaging system shown in FIG. 7.

Figure 1:
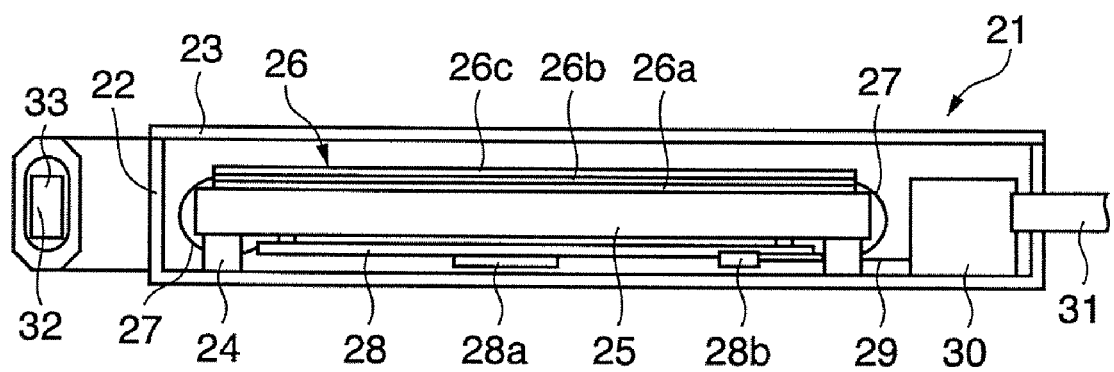
FIG. 1 is a sectional view of an imaging unit according to the first embodiment.

FIG. 1 is a sectional view of an imaging unit 21 according to the first embodiment. A case lid 23 made of a radiolucent material hermetically seals a box-shaped case 22 that is open upward. In the case 22, a base 25 made of a metal is fixed via a support unit 24. An X-ray image detection panel 26 formed by stacking a substrate 26a, photoelectric conversion elements 26b, and fluorescent plate 26c are arranged on the base 25.

A glass plate is often used as the substrate 26a because it needs to be free from chemical actions with a semiconductor element, resist the temperature in the semiconductor process, and have dimensional stability. The photoelectric conversion elements 26b are formed on the substrate 26a in a two-dimensional array by a semiconductor process. The fluorescent plate 26c prepared by applying a metal compound phosphor to a resin plate is integrally bonded to the substrate 26a.

The photoelectric conversion elements 26b are connected, via a flexible circuit plate 27 connected to the side surface, to a circuit board 28 having electronic components 28a and 28b to process an electrical signal obtained by photoelectric conversion. A relay electric circuit unit 30 is connected to the circuit board 28 via a cable 29. The relay electric circuit unit 30 is connected to an external controller (not shown) via a cable 31 to supply a power or transfer a signal.

The imaging unit 21 has a grip unit 32 on its side surface. To detect user's gripping, the grip unit 32 incorporates a grip detector 33 for detecting an electrostatic capacitance or pressure. The output from the grip detector 33 is connected to the circuit board 28. The circuit board 28 outputs the output acquired from the grip detector 33 to the external controller. The external controller releases a lock of the imaging unit 21 upon receiving the output.

The imaging unit 21 acquires an X-ray image by detecting X-rays emitted from an X-ray tube that serves as a radiation generation unit for generating X-rays. When X-rays transmitted through an object (not shown) strike the imaging unit 21 shown in FIG. 1 from above of it, the fluorescent plate 26c emits light. The two-dimensionally arrayed photoelectric conversion elements 26b convert the light into an electrical signal, thereby obtaining a digital image. The obtained digital image is transferred to the relay electric circuit unit 30 via the cable 29 and then immediately transferred to an external monitor via the cable 31.

Figure 2:
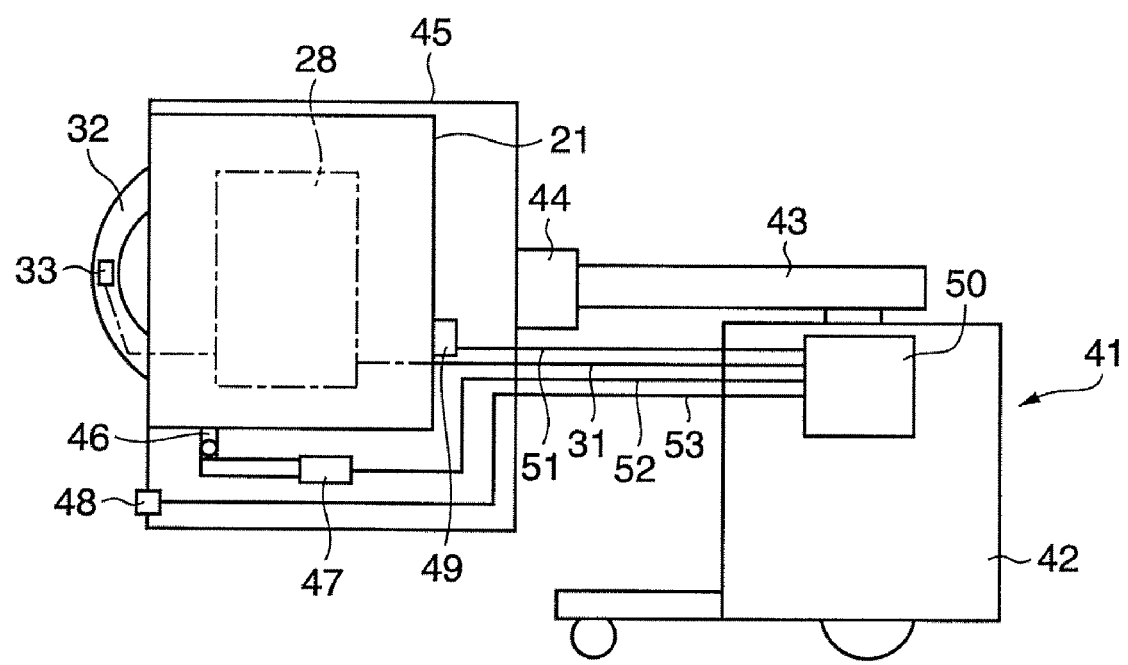
FIG. 2 is a side view of a radiographic imaging apparatus according to the first embodiment.

The imaging unit 21 is used as a cassette independently or combined with various support units. FIG. 2 is a side view of a mobile C-arm radiographic imaging apparatus 41 combined with the imaging unit 21. In the mobile C-arm radiographic imaging apparatus 41, a rotating horizontal shaft 43 is pivotally supported on a main body 42. An arm member 44 is attached to the distal end of the rotating horizontal shaft 43. A holder unit 45 which detachably includes the imaging unit 21 is fixed at the distal end of the arm member 44. The holder unit 45 has a lock member 46 to restrict detachment of the imaging unit 21 and an actuator 47 to drive the lock member 46. The holder unit 45 also has an operation switch 48 to make the operator detach the imaging unit 21 and a detector 49 to detect the attachment of the imaging unit 21.

The main body 42 incorporates a controller 50 including a CPU which mainly sets conditions of the X-ray generator and control the C-arm moving part. The grip detector 33, detector 49, actuator 47, and operation switch 48 are connected to the controller 50 via the cables 31, 51, 52, and 53, respectively.

Figure 3:
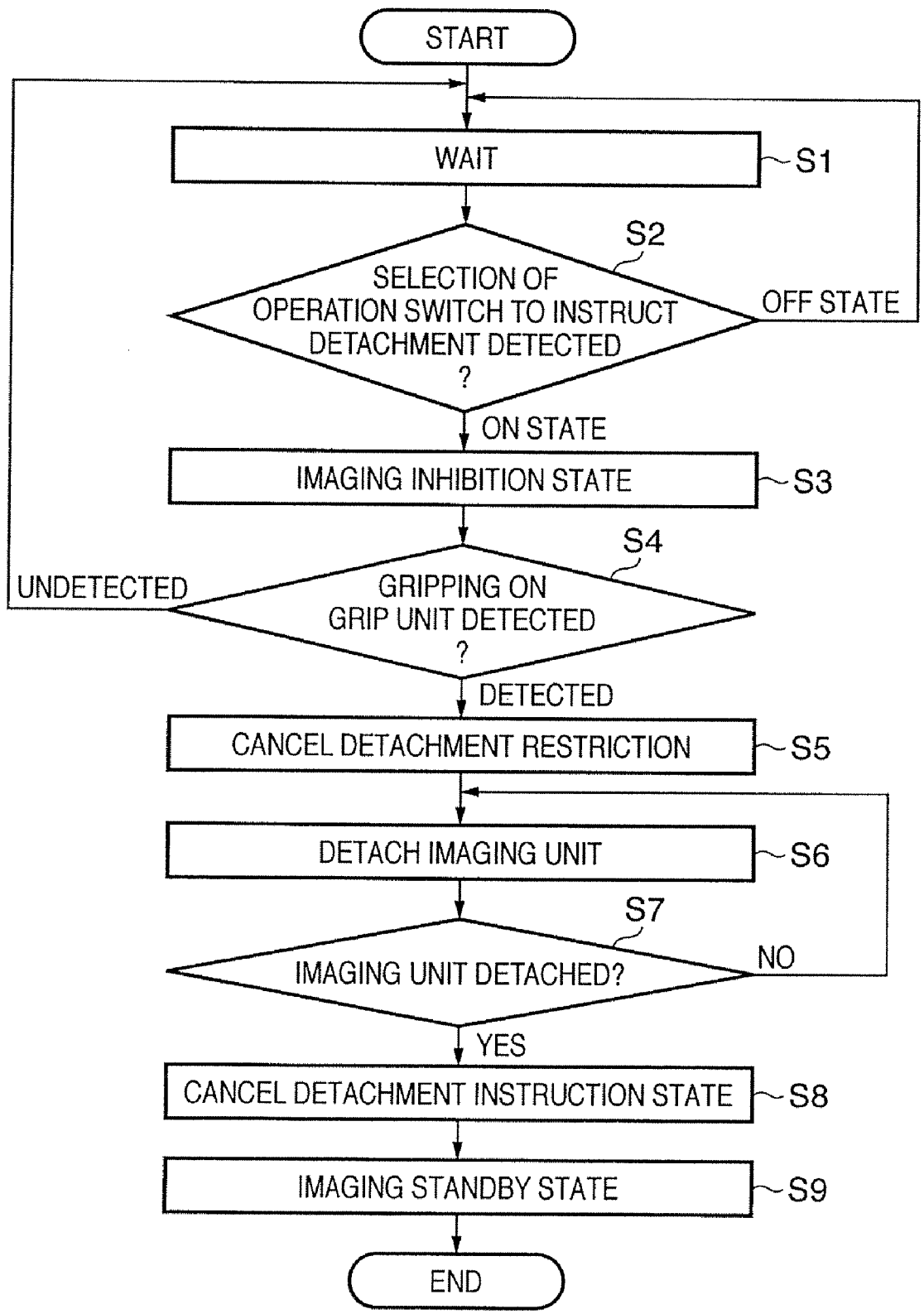
FIG. 3 is a flowchart of an operation of detaching the imaging unit according to the first embodiment.

FIG. 3 is a flowchart illustrating an operation process of the radiographic imaging apparatus 41 in an operation of detaching the imaging unit 21. In step S1, the radiographic imaging apparatus 41 waits for a predetermined time in an imaging preparatory state. In step S2, the controller 50 detects whether the operation switch 48, adapted to instruct detachment of the imaging unit 21, is selected. If the operation switch 48 is OFF, the controller 50 determines that the imaging preparatory state is maintained, and the process returns to step S1. If the operation switch 48 is selected, and its ON state is detected, the process advances to step S3 to inhibit imaging. More specifically, the operation of an exposure switch to generate X-rays or access to imaging condition settings on a C-arm console is inhibited.

In step S4, the controller 50 detects based on a detection signal from the grip detector 33 whether the user grips the grip unit 32. If user's gripping on the grip unit 32 is detected ("detected" in step S4), the process advances to step S5. The controller 50 controls and drives the actuator 47 to cancel the detachment restriction by the lock member 46. If gripping on the grip unit 32 is not detected in step S4 ("undetected" in step S4), the process returns to step S1.

If a predetermined time enough for the operator to detach the imaging unit 21 elapses in step S6, the imaging unit 21 is detached, and the process advances to step S7. The controller 50 detects based on a signal from the detector 49 whether the imaging unit 21 is detached. If detachment of the imaging unit 21 is detected ("YES" in step S7), the process advances to step S8. The controller 50 cancels the detachment instruction state set by the operation switch 48. The process advances to step S9 to set the imaging standby state again. If the imaging unit 21 is not detached in step S7 ("NO" in step S7), the process returns to step S6.

In this system configuration, the user cannot detach the imaging unit 21 without reliably gripping the grip unit 32 in the holder unit 45. It is therefore possible to reduce the risk of erroneously dropping the imaging unit 21.

Figure 4:
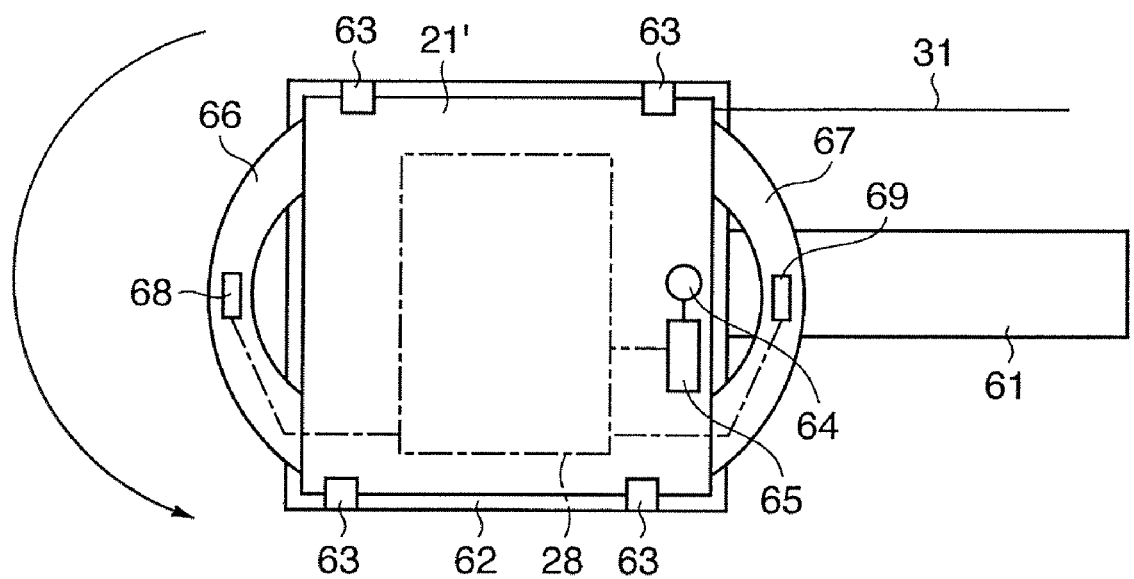
FIG. 4 is a view of the support unit of an imaging unit according to the second embodiment.

FIG. 4 is a view showing the arrangement of a radiographic imaging apparatus according to the second embodiment. The mechanism for detachably supporting an imaging unit 21' is the same as in the first embodiment, and a description thereof will not be repeated. FIG. 4 shows a state wherein an arm member 61 of a C-arm is horizontal.

The arm member 61 has, at its distal end, a holder unit 62 to hold the imaging unit 21'. A plurality of lock members 63 to hold the imaging unit 21' are provided around the holder unit 62. When the attached imaging unit 21' rotates in the direction of the arrow, the restriction by the lock members 63 is canceled. The holder unit 62 itself can also rotate in the direction of the arrow. As in FIG. 2, a controller can switch the rotational movement enable/disable state of the holder unit 62.

On the other hand, the imaging unit 21' incorporates a restriction pin member 64 movable in the radiation direction of the image reception area and an actuator 65 to drive the restriction pin member 64 so that the rotation restriction of the imaging unit 21' can be ON/OFF-controlled. The imaging unit 21' has grip units 66 and 67 on both sides, which incorporate grip detectors 68 and 69, respectively. The imaging unit 21' also has an attachment detector to detect its attachment. The outputs from the grip detectors 68 and 69 are connected to a circuit board 28 in the imaging unit 21' and output to the outside via a cable 31.

In attaching the imaging unit 21' to the holder unit 62, when the imaging unit 21' is pressed against the holder unit 62 in the radiation direction of the image reception area of the imaging unit 21', the lock members 63 lock the imaging unit 21'. At this time, when the user releases the grip units 66 and 67, gripping detection is turned off. Rotation restriction by the restriction pin member 64 and rotation restriction of the holder unit 62 are turned on.

In the radiographic imaging apparatus according to the second embodiment, the operator can execute two operations on the imaging unit 21'. In the first operation mode, the operator grips one of the grip units 66 and 67 of the imaging unit 21' and rotates it together with the holder unit 62, thereby positioning the imaging unit 21' to a desired angle. In the second operation mode, the operator rotates the imaging unit 21' and detaches it from the holder unit 62. That is, switching between the two operation modes is done depending on the manner the operator grips the grip units 66 and 67.

Figure 5:
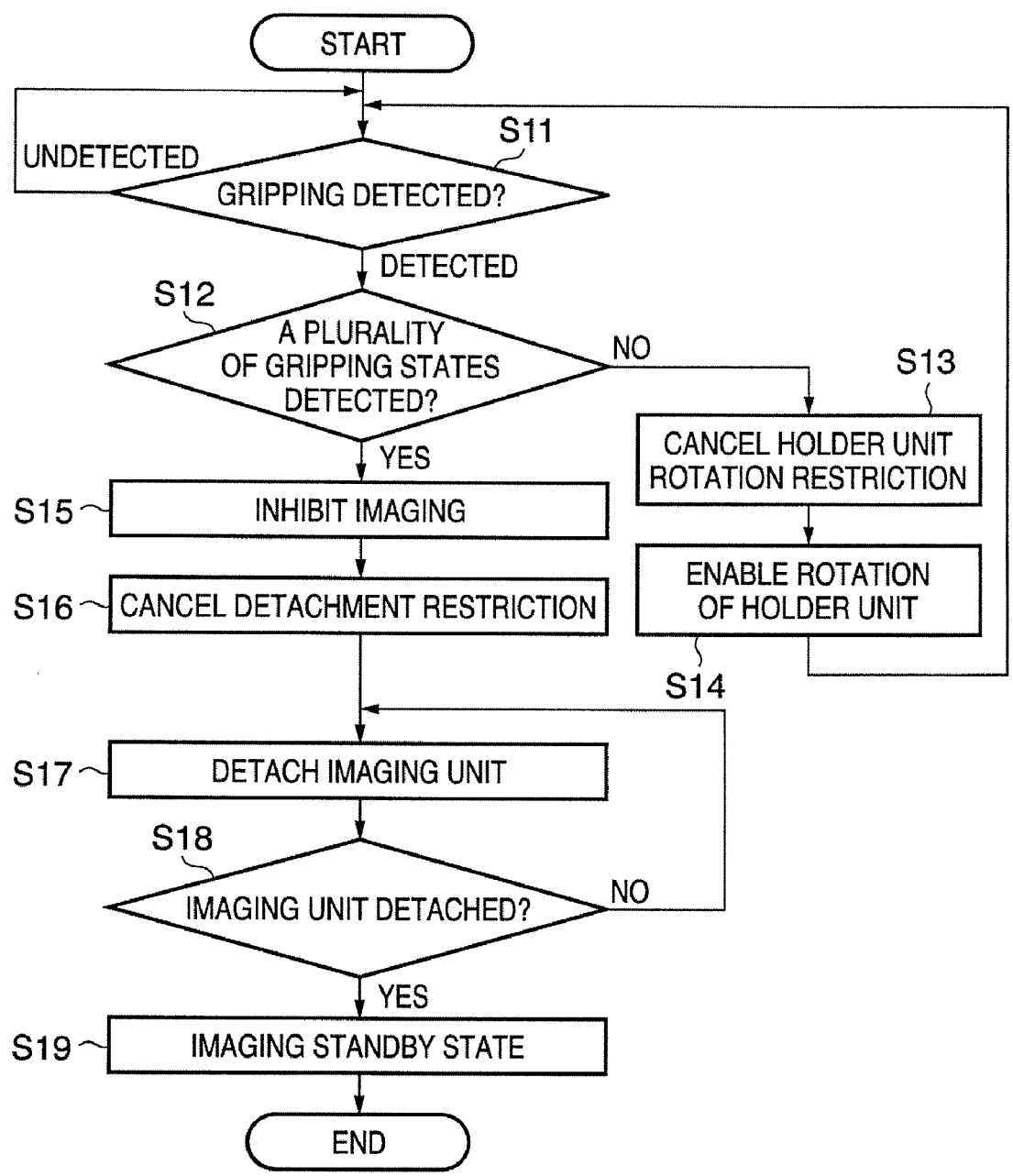
FIG. 5 is a flowchart of an operation of detaching the imaging unit according to the second embodiment.

FIG. 5 is a flowchart illustrating an operation process of switching the above-described two operations in the radiographic imaging apparatus according to the second embodiment. In step S11, the controller determines whether the grip detectors 68 and 69 in the grip units 66 and 67 of the imaging unit 21' detect the operator's gripping. If gripping on the grip units 66 and 67 is detected ("detected" in step S11), the process advances to step S12. Otherwise ("undetected" in step S11), the process returns to step S11.

In step S12, the controller 4 determines whether a plurality of gripping states are detected in step S11. If one gripping state is detected ("N" in step S12), the controller determines it as rotation for imaging in the first operation mode. The process advances to step S13. In step S13, the rotation restriction of the holder unit 62 is canceled. In step S14, the holder unit 62 is made rotatable by the operator, and the process returns to step S11.

If a plurality of gripping states are detected in step S12 ("Y" in step S12), the controller determines it as an operation of detaching the imaging unit 21' in the second operation mode. In step S15, the controller controls to inhibit imaging. In step S16, the controller drives the actuator 65 to move the restriction pin. This enables rotation of the imaging unit 21' and cancels detachment restriction including removal restriction. In step S17, the operator who grips the grip units 66 and 67 moves the imaging unit 21' in the rotational direction. Since rotation of the holder unit 62 itself is restricted, the imaging unit 21' and holder unit 62 move relative to each other. The lock members 63 are unlocked to allow detachment. The operator detaches the imaging unit 21', and the process advances to step S18. Note that although step S17 is not the operation of the radiographic imaging apparatus, the process is illustrated for the descriptive convenience.

In step S18, the controller determines based on a signal from the attachment detector whether the imaging unit 21' is detached. If the controller determines that the imaging unit 21' is detached ("YES" in step S18), the process advances to step S19. The controller sets the radiographic imaging apparatus in the imaging standby state. If it is determined in step S18 that the imaging unit 21' is not detached ("NO" in step S18), the process returns to step S17.

To change the angle of the imaging unit 21' as in the first operation mode, the operator grips one grip unit. That is, when the single grip detector 68 or 69 detects gripping, the controller drives the actuator 65 to move the restriction pin member 64, thereby canceling rotation restriction. Conversely, to detach the imaging unit 21', the operator grips both the grip units 66 and 67 to reduce the risk of dropping the imaging unit 21'. That is, the controller cancels detachment restriction when both the grip detectors 68 and 69 detect gripping.

Figure 6:
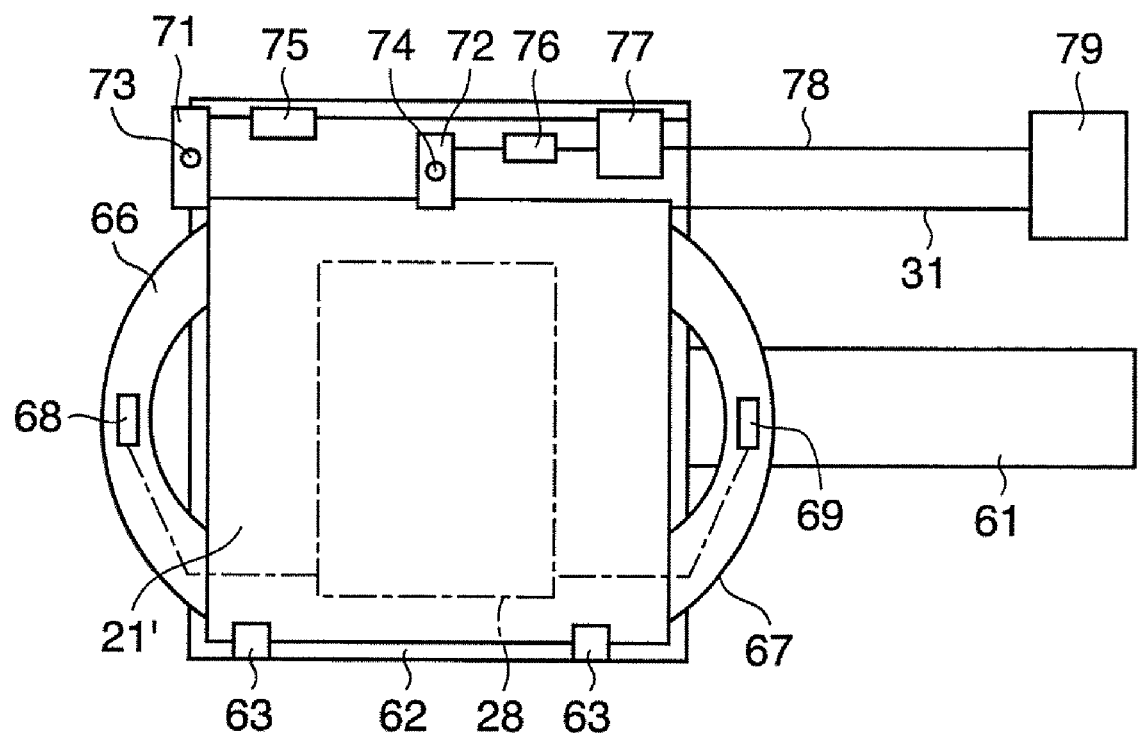
FIG. 6 is a view of an imaging unit according to the third embodiment.
Figure 7:
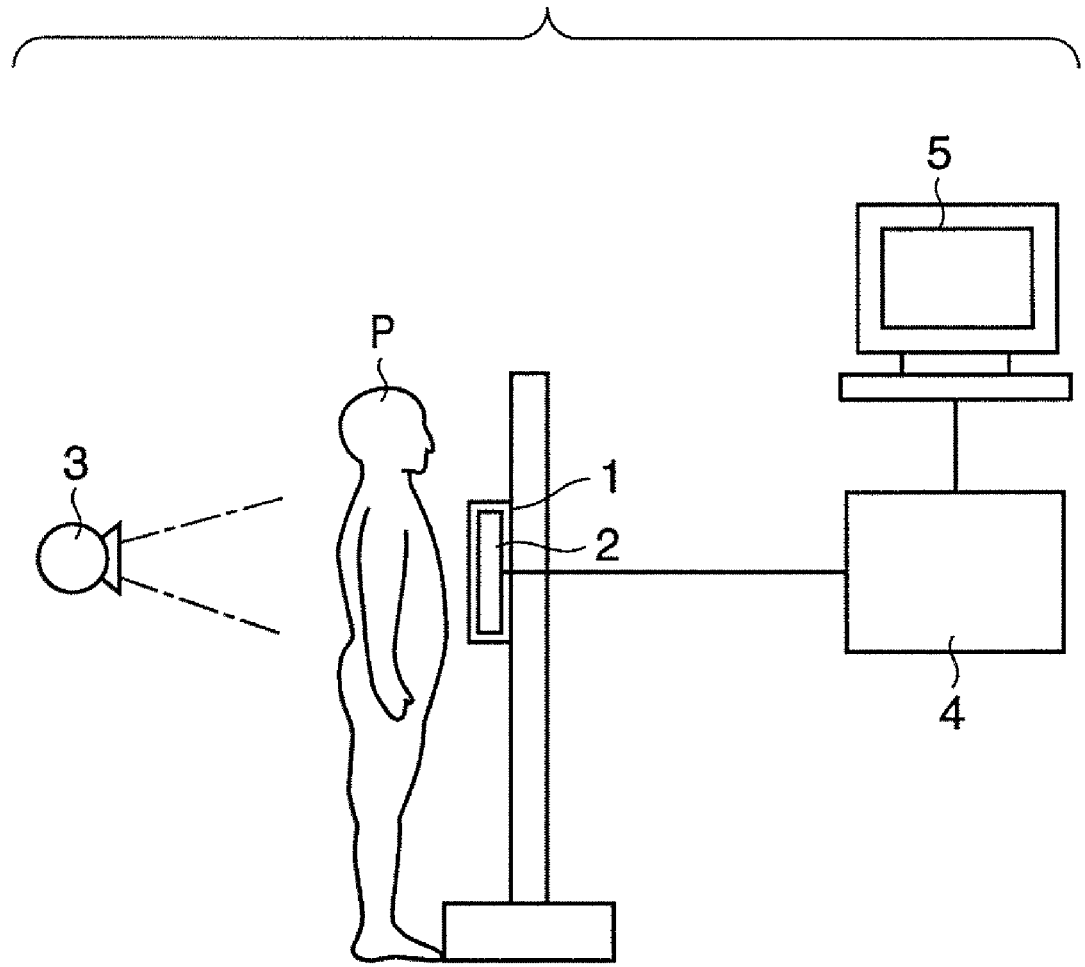
FIG. 7 is a schematic view of a system using a radiographic imaging apparatus.

FIG. 6 is a view showing the arrangement of a radiographic imaging apparatus according to the third embodiment. The mechanism for detachably supporting an imaging unit is almost the same as in the above-described embodiments. The same reference numerals as in FIG. 4 denote the same members in FIG. 6.

A holder unit 62 has lock members 71 and 72 to hold an imaging unit 21'. The lock member 71 capable of pivoting about a shaft 73 restricts the horizontal movement of the imaging unit 21' to the left side. On the other hand, the lock member 72 capable of pivoting about a shaft 74 restricts movement in a direction normal to the image reception area of the imaging unit 21'. The lock members 71 and 72 are connected to actuators 75 and 76, respectively. The actuators 75 and 76 are connected to a controller 79 mounted on an external support unit via a control board 77 and cable 78. The imaging unit 21' has two grip units 66 and 67, as in the second embodiment. Grip detectors 68 and 69 are connected to the controller 79 via a circuit board 28 and cable 31.

Upon detecting gripping on only the grip unit 66 of the imaging unit 21', the information is sent to the controller 79. The controller 79 outputs an actuator driving instruction to drive the actuator 75 and cancel the restriction by the lock member 71 interlockingly. This allows to pull the imaging unit 21' horizontally to the left side (i.e., direction parallel to the image reception area of the imaging unit 21') in the first operation mode.

On the other hand, when the user grips both the grip units 66 and 67, the controller 79 outputs an actuator driving instruction to drive the actuator 76 and make the lock member 72 pivot. This allows to detach the imaging unit 21' in the direction normal to its image reception area in the second operation mode.

Figure 8:
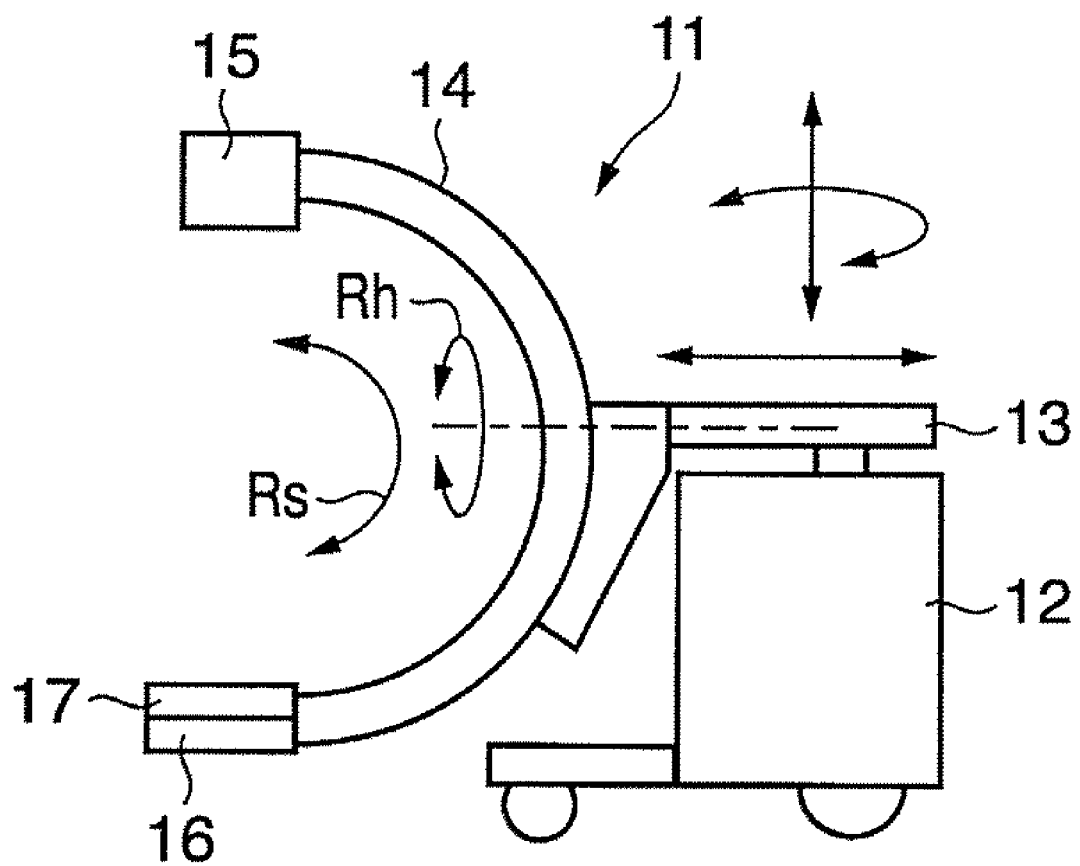
FIG. 8 is a view of the arrangement of a conventional mobile C-arm radiographic imaging apparatus.

A support unit including an arm member 61 has a sensor to recognize the position information of the arm member 61. For example, when a C-arm shown in FIG. 8 of the prior art is used, the arm member 61 corresponds to the arm member 14. Rotation Rh about a horizontal shaft and rotation Rs along the track of the arm itself determine the posture of the imaging unit 21'. The controller 79 monitors angle information in every rotation and automatically calculates the posture of the imaging unit 21'.

The mode that enables detachment of the imaging unit 21' is set in advance in the controller 79 depending on the posture of the imaging unit 21'. example, in the first operation mode to horizontally pull the imaging unit 21', the operator grips it by one hand. If the imaging unit 21' is pulled downward, it may drop. Hence, the controller 79 inhibits detachment. Conversely, if the imaging unit 21' which is located on the lower side is pulled upward, the operator cannot grip it by both hands. Hence, the controller 79 controls to inhibit the second operation mode and enable only the first operation mode.

In this arrangement, the apparatus side selects the mode in advance depending on the posture of the holder unit 62 so that the risk of erroneously dropping the imaging unit 21' can be reduced.

The holder unit 62 to be combined is not limited to the imaging table. The same arrangement is applicable to even a stand for a standing position or a universal stand.

The preferred embodiments of the present invention have been described above. The present invention is not limited to the embodiments, and various changes and modifications can be made within the spirit and scope of the present invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-283931, filed Oct. 18, 2006 which is hereby incorporated by reference herein in its entirety.

What is claimed is:

1. A radiographic imaging apparatus comprising:
   a holding unit which holds an imaging unit for detecting radiation generated by a radiation generation unit and acquiring a radiographic image;
   a detachment restriction unit which restricts detachment of the imaging unit from the holding unit; and
   a controller which cancels the restriction by the detachment restriction unit,
   wherein the imaging unit has two grip detection units, and the controller cancels a rotation restriction of the holding unit when one of the two grip detection units detects a gripping on the imaging unit and cancels a detachment restriction by the detachment restriction unit when the two grip detection units detect the gripping on the imaging unit.

2. The apparatus according to claim 1, further comprising:
   a support unit which supports the holding unit; and
   a recognition unit which recognizes a position of the support unit, wherein the controller determines based on position information from the recognition unit whether to cancel the restriction by the detachment restriction unit.

3. The apparatus according to claim 1, further comprising a switch configured to input a detachment instruction of the imaging unit, wherein said controller cancels the restriction by the detachment restriction unit in a case that the grip detection units for detecting gripping of the imaging unit detects the gripping on the imaging unit and the detachment instruction of the imaging unit is input by the switch.

4. An imaging unit for acquiring a radiographic image comprising:
   a holding unit which holds an imaging unit for detecting radiation generated by a radiation generation unit and acquiring a radiographic image;
   a detachment restriction unit which restricts detachment of the imaging unit from the holding unit;
   a grip unit having two grip detection units each configured to detect a gripping on the imaging unit; and
   an output unit which outputs a signal to a controller for releasing a lock of the imaging unit,
   wherein the controller cancels a rotation restriction of the holding unit when one of the two grip detection units detects the gripping on the imaging unit and cancels a detachment restriction by the detachment restriction unit when the two grip detection units detect the gripping on the imaging unit.

5. A radiographic imaging system comprising:
   a holding unit which holds an imaging unit for detecting radiation generated by a radiation generator and acquiring a radiographic image;
   a restriction unit which has a first restriction mode to restrict detachment of the imaging unit for acquiring the radiographic image in a direction parallel to an image reception area of the imaging unit and a second restriction mode to restrict detachment of the imaging unit in a direction perpendicular to the image reception area of the imaging unit; and
   a controller which cancels the restriction by the restriction unit,
   wherein the imaging unit has two grip detection units, and the controller cancels the first restriction mode of the restriction unit when one of the two grip detection units detects a gripping on the imaging unit and cancels the second restriction mode by the restriction unit when the two grip detection units detect the gripping on the imaging unit.

6. The system according to claim 5, wherein the controller determines based on an orientation of the imaging unit whether to cancel the restriction in the first restriction mode and the second restriction mode.

* * * * *